(12) United States Patent
Shin et al.

(10) Patent No.: US 11,857,237 B2
(45) Date of Patent: Jan. 2, 2024

(54) FORCEPS FOR INTERNAL FIXATION

(71) Applicant: THE CATHOLIC UNIVERSITY OF KOREA INDUSTRY—ACADEMIC COOPERATION FOUNDATION, Seoul (KR)

(72) Inventors: Seung Han Shin, Seoul (KR); Yang Guk Chung, Seoul (KR); Do Kun Yoon, Suwon-si (KR); Moo Sub Kim, Gimhae-si (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 331 days.

(21) Appl. No.: 17/424,750

(22) PCT Filed: Dec. 23, 2019

(86) PCT No.: PCT/KR2019/018293
§ 371 (c)(1),
(2) Date: Jul. 21, 2021

(87) PCT Pub. No.: WO2020/153615
PCT Pub. Date: Jul. 30, 2020

(65) Prior Publication Data
US 2022/0133378 A1  May 5, 2022

(30) Foreign Application Priority Data
Jan. 24, 2019 (KR) .......... 10-2019-0009330

(51) Int. Cl.
*A61B 17/88* (2006.01)
*A61B 17/80* (2006.01)

(52) U.S. Cl.
CPC ........ *A61B 17/8866* (2013.01); *A61B 17/808* (2013.01)

(58) Field of Classification Search
CPC .................... A61B 17/8866; A61B 17/808
See application file for complete search history.

(56) References Cited

U.S. PATENT DOCUMENTS

| | | | |
|---|---|---|---|
| 4,790,302 | A | 12/1988 | Colwill et al. |
| 5,849,012 | A | 12/1998 | Abboudi |
| 8,936,615 | B2 | 1/2015 | Pappalardo et al. |
| 9,642,641 | B2 * | 5/2017 | Fernandez Dell'oca ..................... A61B 17/282 |
| 2017/0252081 | A1 | 9/2017 | Felder et al. |

FOREIGN PATENT DOCUMENTS

| | | |
|---|---|---|
| KR | 20110038692 | 4/2011 |
| KR | 20120111084 | 10/2012 |

OTHER PUBLICATIONS

International Search Report—PCT/KR2019/018293 dated Apr. 6, 2020.

\* cited by examiner

*Primary Examiner* — Si Ming Ku
(74) *Attorney, Agent, or Firm* — CANTOR COLBURN LLP

(57) ABSTRACT

Provided is forceps for internal fixation, including: a first member having a first holding portion for holding a first side of bone fragments and a first grip extending from the first holding portion; and a second member having a second holding portion for holding a second side spaced a predetermined distance from the first side of the bone fragments and a second grip extending from the second holding portion.

11 Claims, 4 Drawing Sheets

FORCEPS FOR INTERNAL FIXATION

TECHNICAL FIELD

The present disclosure relates to forceps for internal fixation which can simultaneously and effectively hold bone fragments and a third member that is used for internal fixation.

BACKGROUND ART

In order to unite bones fractured due to an injury or cut for correction, the bone fragments are put together and then fixed by a third member and a screw, etc. This procedure is called internal fixation (osteosynthesis) and restoring displaced bone fragments into their original shape is called reduction.

In detail, internal fixation is a surgical operation of fixing bone fragments by driving screws into screw holes formed in a third member made of metal with the third member placed in the longitudinal direction of the bone across the fracture line or cut line of the bone.

In relation to internal fixation, there is Korean Patent Application Publication No. 10-2012-0111084 (titled, "Supporting clamp for region of the fracture).

Existing clamps including the patent have a structure that holds two bone fragments without interfering with a third member, so there is a problem that they cannot simultaneously hold a third member and bone fragments, and as a result, there is a problem that it is difficult to bring a third member in close contact with bone fragments.

Further, they have a drawback that additional peel off of soft tissues from the bone is necessary in order to apply the clamp to the fracture site or the cut site of the bone.

That is, is the method of using the clamp according to the related art has a problem that it is difficult to accurately place a third member on the outer surface of a bone due to variation of the outer surface of bones. Further, when soft tissues are peeled off from the fracture site or cut site of a bone blood flow is blocked and thus bone union is hindered. soft tissue peeling also increases surgery time.

Therefore, the clamp decreases precision of placing a third member and the accuracy of reducing bone fragments, which may adversely influence the surgery result.

DISCLOSURE

Technical Problem

The present disclosure has been made in an effort to solve the problems and an objective of the present disclosure is to provide forceps for internal fixation which can effectively perform internal fixation by simultaneously and tightly holding two bone fragments and a third member.

Another objective of the present disclosure is to provide forceps for internal fixation which is designed in consideration of directionality to be able to tightly hold two bone fragments and a third member even if only the skin and the muscle in the placing direction of a third member are partially cut.

Technical Solution

In order to achieve the objectives, the present disclosure provides forceps for internal fixation which includes: a first member having a first holding portion for holding a first side of bone fragments and a first grip extending from the first holding portion; and a second member having a second holding portion for holding a second side spaced a predetermined distance from the first side of the bone fragments and a second grip extending from the second holding portion.

An inner surface of the first holding portion may be formed to correspond to the first side of the bone fragments and an inner surface of the second holding portion may be formed to correspond to the second side of the bone fragments.

A prominence-depression portion may be formed on a portion or the entire of the inner surface of the first holding portion or the inner surface of the second holding portion.

The forceps may further include a third member that is disposed on a third side of the bone fragments between the first side and the second side of the bone fragments and is screw-fastened to the third side of the bone fragments.

An inner surface of the third member may be formed to correspond to the shape of the third side of the bone fragments.

The first member may further have a first fixing portion fixing a portion of the third member to the third side of the bone fragments between the first holding portion and the first grip, and the second member may further have a second fixing portion fixing the other portion of the third member to the third side of the bone fragments between the second holding portion and the second grip.

The first fixing portion may extend from the first holding portion in a shape corresponding to a portion of the third member and the second fixing portion may extend from the second holding portion in a shape corresponding to the shape of the other portion of the third member.

The first fixing portion may have a first fixing member having a side having a shape corresponding to a portion of the third member, and a first elastic member disposed between another side of the first fixing member and the first holding portion or between another side of the first fixing member and the first grip and applying pressure to the first fixing member; and the second fixing portion may have a second fixing member having a side having a shape corresponding to the other portion of the third member, and a second elastic member disposed between another side of the second fixing member and the second holding portion or between another side of the second fixing member and the second grip and applying pressure to the second fixing member.

The first member may further have a coupling groove formed on an inner surface of the first grip and the second member may further have a coupling protrusion formed on an inner surface of the second grip to face the coupling groove and configured to be fitted in the coupling groove.

The coupling protrusion and the coupling groove each may be formed at least two positions to face each other, respectively.

The forceps may further include a fourth member retaining the first grip and the second grip, thereby providing a fixing force to the first member and the second member.

The first grip and the second grip may be narrowed toward free ends.

At least one or more first fixing protrusions may be formed on an outer surface of the first grip, at least one or more second fixing protrusions may be formed on an outer surface of the second grip, and fixing grooves corresponding to the first fixing protrusion and the second fixing protrusion may be formed on an inner surface of the fourth member.

Advantageous Effects

According to the present disclosure, it is possible to tightly hold two bone fragments and the third member for the structural characteristics of the first member and the second member, thereby being able to precisely place the third member to the bone fragments.

Further, since it is possible to move the first member and the second member in the placing direction of the third member and hold bone fragments and the third member, it is possible to perform internal fixation after partially cutting only the skin and the muscle in the placing direction of the third member.

MODE FOR INVENTION

Figure 1:
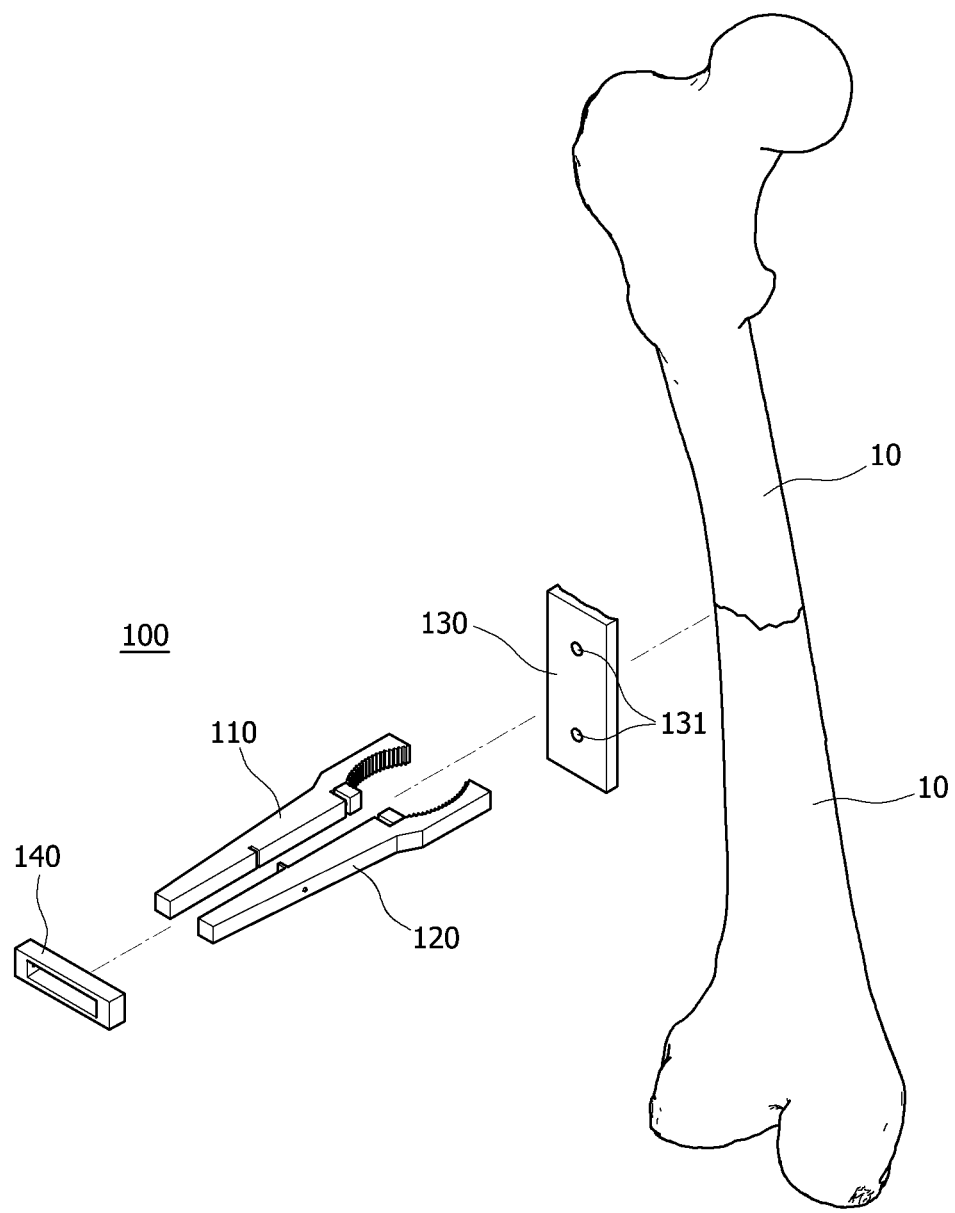
FIG. 1 is a view showing forceps for internal fixation according to an embodiment of the present disclosure before it is assembled.

Hereinafter, exemplary embodiments of the present disclosure will be described in detail with reference to the accompanying drawings.

All terms used herein are the same as general meanings of terms that those skilled in the art understand unless specifically defined, and if terms used herein have meanings conflicting with general meanings of the terms, the definition used herein has priority.

However, the following description is provided to describe embodiments of the present disclosure without limiting the scope of the present disclosure, and same reference numerals used throughout the specification indicate the same components.

Figure 2:
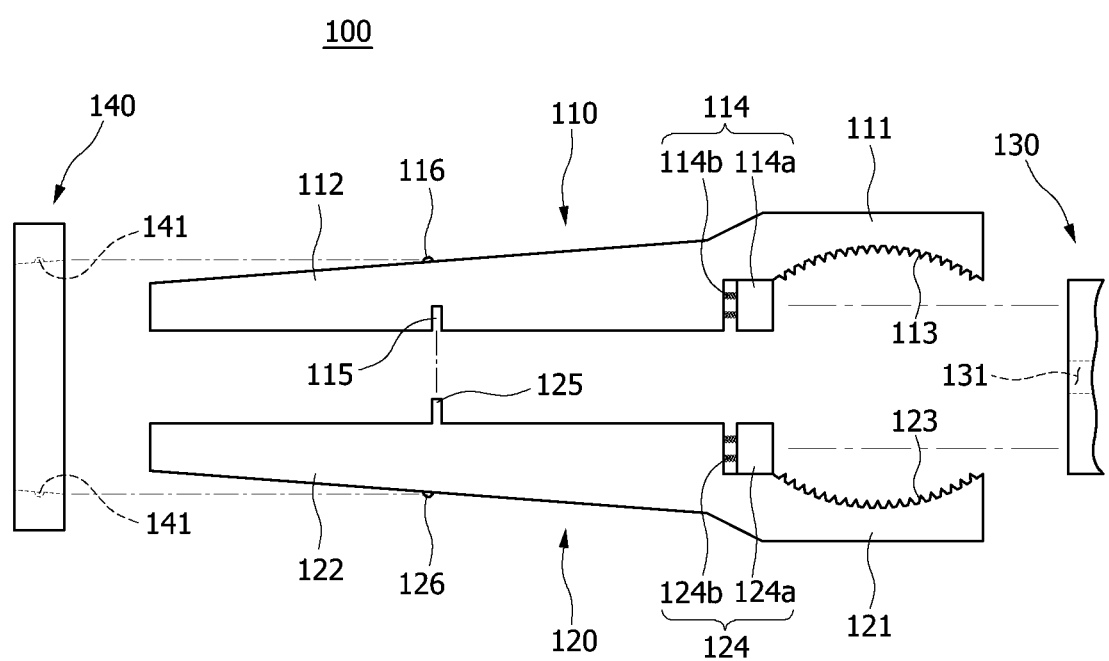
FIG. 2 is a top view of the forceps for internal fixation according to an embodiment of the present disclosure.
Figure 3:
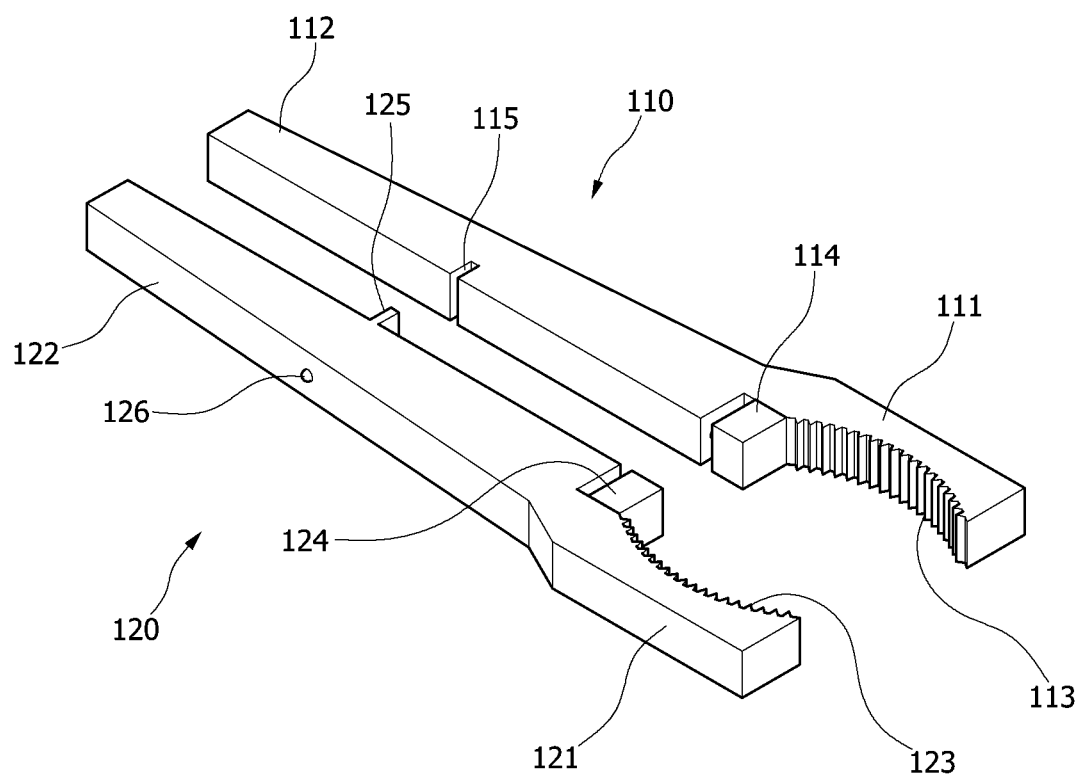
FIG. 3 is a perspective view of a first member and a second member according to an embodiment of the present disclosure.
Figure 4:
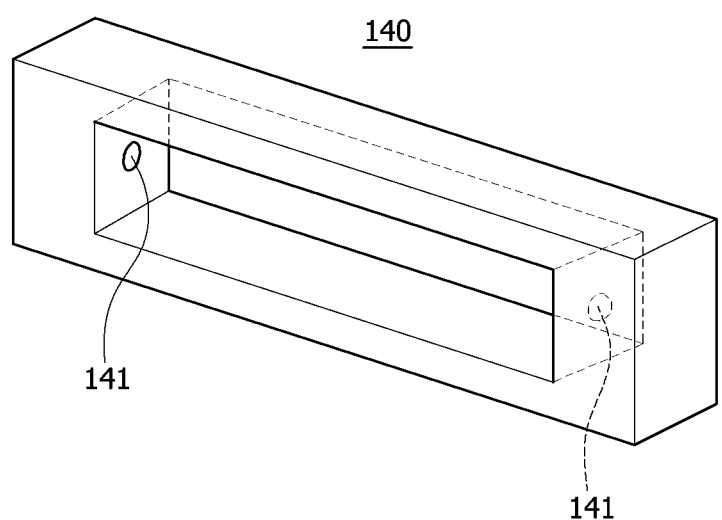
FIG. 4 is a perspective view of a fourth member according to an embodiment of the present disclosure.

FIG. 1 is a view showing forceps for internal fixation according to an embodiment of the present disclosure before it is assembled, FIG. 2 is a top view of the forceps for internal fixation according to an embodiment of the present disclosure, FIG. 3 is a perspective view of a first member and a second member according to an embodiment of the present disclosure, and FIG. 4 is a perspective view of a fourth member according to an embodiment of the present disclosure.

Hereinafter, exemplary embodiments of the present disclosure will be described in detail with reference to the accompanying drawings.

All terms used herein are the same as general meanings of terms that those skilled in the art understand unless specifically defined, and if terms used herein have meanings conflicting with general meanings of the terms, the definition used herein has priority.

However, the following description is provided to describe embodiments of the present disclosure without limiting the scope of the present disclosure, and same reference numerals used throughout the specification indicate the same components.

Referring to FIGS. 1 to 4, forceps 100 for internal fixation according to an embodiment of the present disclosure, in a broad meaning, may include a first member 110, a second member 120, and a third member 130, and may further include a fourth member 140.

In order to more clearly describe the technical characteristics of the present disclosure before describing the configuration of the present disclosure, the direction in which the forceps 100 for internal fixation according to an embodiment is moved toward bone fragments 10 is defined as a front direction, the opposite direction is defined as a rear direction. Further, the direction going to a first member 110 to be described below is defined as a left direction and the direction going to a second member 120 to be described below is defined as a direction.

The surfaces facing each other of the first member 110 and the second member 120 to be described below are defined as inner surfaces.

The first member 110 may have a first holding portion 111 for holding a first side of the bone fragment 10 and a first grip 112 extending from the first holding portion 111.

The second member 120 may have a second holding portion 121 for holding a second side spaced a predetermined distance from the first side of the bone fragment 10 and a second grip 122 extending from the second holding portion 121.

The first member 110 and the second member 120 are provided in a pair, thereby being able to achieve the function of forceps for holding the bone fragments 10 and a third member 130 to be described below.

The first side and the second side of the bone fragment 10 may be both sides of a third side of the bone fragment 10 to which the third member 130 to be described below is placed.

In the forceps 100 for internal fixation according to an embodiment of the present disclosure, the inner surface of the first holding portion 111 may be formed to correspond to the first side of the bone fragment 10 and the inner surface of the second holding portion 121 may be formed to correspond to the second side of the bone fragment 10.

That is, the forceps 100 for internal fixation according to an embodiment of the present disclosure may function as customized forceps, depending on detailed shapes of bone fragments 10 photographed by medical equipment, and the inner surface of the first holding portion 111 and the inner surface of the second holding portion 121 can accurately hold desired portions of the bone fragment 10, so it is possible to more precisely place the third member 130 to be described below to a desired position.

In order to match the shapes of the inner surface of the first holding portion 111 and the inner surface of the second holding portion 121, the first member 110 and the second member 120 according to an embodiment of the present disclosure may be formed through a 3D printer on the basis of data based on the detailed shapes of the bone fragments 10 photographed by medical equipment.

A prominence-depression portion 113, 123 is formed on a portion or the entire of the inner surface of the first holding portion 111 or the inner surface of the second holding portion 121, so the forceps can tightly hold the bone fragment 10. The prominence-depression portions 113 and 123, as shown in the figures, may be longitudinally elongated, but are not limited thereto and may be formed in a protrusion shape.

In other words, the first member 110 and the second member 120 may be formed to entirely correspond to each other in a pair, but the inner surface of the first holding portion 111 and the inner surface of the second holding portion 121 may be formed in different shapes, depending on the shapes of the bone fragments 10.

The third member 130, which is disposed on the third side of the bone fragment 10 between the first side and the second side of the bone fragment 10 and is screw-fastened to the third side of the bone fragment 10, may be generally referred to as a metal plate or a plate.

Accordingly, the third member 130 may have one or more fastening holes 131 at two sides.

The third member 130 according to an embodiment of the present disclosure, unlike existing metal plate, may have an inner surface (front) formed to correspond to the shape of the third side of the bone fragment 10. Accordingly, the third member 130 can be precisely placed at a position for fixing both bone fragments 10.

For customized shape of the inner surface of the third member 130, the third member 130 according to an embodiment of the present disclosure may be manufactured through a 3D printer on the basis of data based on the detailed shape of the bone fragments 10 photographed by medical equipment.

In order to tightly hold the third member 130 disposed on the third side of the bone fragment 10, the first member 110 may further has a fixing portion 114 that fixes a portion of the third member 130 to the third side of the bone fragment 10 between the first holding portion 111 and the first grip. Further, the second member 120 may further have a second fixing portion 124 that fixes the other portion of the third member 130 to the third side of the bone fragment 10 between the second holding portion 121 and the second grip 122.

The first fixing portion 114 and the second fixing portion 124 may be implemented in two exemplary types.

First, the first fixing portion 114 and the second fixing portion 124 are integrally formed with the first member 110 and the second member 120.

That is, the first fixing portion 114 may extend from the first grip 111 in a shape corresponding to a portion of the third member 130 to be held, and the second fixing portion 124 may extend from the second grip 121 in a shape corresponding to the other portion of the third member 130 to be held.

When the entire forceps for internal fixation according to an embodiment of the present disclosure is formed in a customized type in accordance with the shape of the bone fragment 10, a holding force can be secured in this first embodiment.

Second, the first fixing portion 114 and the second fixing portion 124 are provided independently from the first member 110 and the second member 120.

That is, the first fixing portion 114 may have a first fixing member 114a having a side having a shape corresponding to a portion of the third member 130, and a first elastic member 114b disposed between another side of the first fixing member 114a and the first holding portion 111 or between another side of the first fixing member 114a and the first grip 112 and applying pressure to the first fixing member 114a. That is, the second fixing portion 124 may have a second fixing member 124a having a side having a shape corresponding to the other portion of the third member 130, and a second elastic member 124b disposed between another side of the second fixing member 124a and the second holding portion 121 or between another side of the second fixing member 124a and the second grip 122 and applying pressure to the second fixing member 124b.

According to the second embodiment, there is an effect of pressing the third member 130 forward, that is, toward the bone fragment 10, so the third member 130 can be more precisely placed at a desired position.

The present disclosure may further include a scope for further increasing the holding force.

In detail, the first member 110 may further have a coupling groove 115 formed on the inner surface of the first grip 112 and the second member 120 may further has a coupling protrusion 124 formed on the inner surface of the second grip 122 to face the coupling groove 114 and configured to be fitted in the coupling groove 115.

This structure can prevent the first member 110 and the second member, which hold the first side and the second side of the bone fragment 10, from twisting and moving forward and rearward.

In order to further secure this effect, the coupling protrusion 125 and the coupling groove 115 each may be formed at least two positions to face each other, respectively.

The forceps may further include a fourth member 140 retaining the first grip 112 and the second grip 122, thereby providing a fixing force to the first member 110 and the second member 120. The first member 110 and the second member 120 that hold the bone fragment 10 can be firmly fixed by the fourth member 140.

In order to further secure the holding force, the first grip 112 and the second grip 112 may be narrowed toward the free ends, and the inner surface of the fourth member 140 may be formed to correspond to the first member 110 and the second member 120, thereby being able to achieve the coupling force by a wedge.

In order to further increase the holding force, at least one or more first fixing protrusions 116 may be formed on the outer surface of the first grip 112, at least one or more second fixing protrusions 126 may be formed on the outer surface of the second grip 122, and fixing grooves 141 corresponding to the first fixing protrusion 116 and the second fixing protrusion 126 may be formed on the inner surface of the fourth member 140.

In short, the present disclosure has a structure being able to perform surgery after partially cutting the skin and the muscle to place the third member 130 to the bone fragments 10 and holds not only bone fragments 10 to be reduced, but the third member 130, thereby being able to perform more precise surgery.

It would be understood by those skilled in the art that the present disclosure may be changed and modified in various ways without departing from the spirit of the present disclosure, and the scope of the present disclosure is not limited to those described in the embodiments and should be determined by claims and equivalent ranges.

The invention claimed is:

1. A forceps for internal fixation, comprising:
    a first member having a first holding portion for holding a first side of bone fragments and a first grip extending from the first holding portion;
    a second member having a second holding portion for holding a second side spaced a predetermined distance from the first side of the bone fragments and a second grip extending from the second holding portion; and
    a third member that is configured to be disposed on a third side of the bone between the first side and the second side of the bone and is configured to be thread-fastened to the third side of the bone,
    wherein the first member further has a first fixing portion for fixing a portion of the third member to the third side of the bone between the first holding portion and the first grip, and the second member further has a second fixing portion for fixing the other portion of the third member to the third side of the bone between the second holding portion and the second grip.

2. The forceps of claim 1, wherein an inner surface of the first holding portion is formed to correspond to the first side of the bone fragments and an inner surface of the second holding portion is formed to correspond to the second side of the bone fragments.

3. The forceps of claim 1, wherein a prominence-depression portion is formed on a portion or the entire of an inner surface of the first holding portion or an inner surface of the second holding portion.

4. The forceps of claim 1, wherein an inner surface of the third member is formed to correspond to the shape of the third side of the bone fragments.

5. The forceps of claim 1, wherein the first fixing portion extends from the first holding portion in a shape corresponding to a portion of the third member and the second fixing portion extends from the second holding portion in a shape corresponding to the shape of the other portion of the third member.

6. The forceps of claim 1, wherein the first fixing portion has a first fixing member having a side having a shape corresponding to a portion of the third member, and a first elastic member disposed between another side of the first fixing member and the first holding portion or between another side of the first fixing member and the first grip and applying pressure to the first fixing member; and the second fixing portion has a second fixing member having a side having a shape corresponding to the other portion of the third member, and a second elastic member disposed between another side of the second fixing member and the second holding portion or between another side of the second fixing member and the second grip and applying pressure to the second fixing member.

7. The forceps of claim 1, wherein the first member further has a coupling groove formed on an inner surface of the first grip and the second member further has a coupling protrusion formed on an inner surface of the second grip to face the coupling groove and configured to be fitted in the coupling groove.

8. The forceps of claim 7, wherein the coupling protrusion and the coupling groove are each formed at at least two positions to face each other, respectively.

9. The forceps of claim 1, further comprising a fourth member retaining the first grip and the second grip, thereby providing a fixing force to the first member and the second member.

10. The forceps of claim 9, wherein the first grip and the second grip are narrowed toward free ends.

11. The forceps of claim 9, wherein at least one or more first fixing protrusions are formed on an outer surface of the first grip, at least one or more second fixing protrusions are formed on an outer surface of the second grip, and fixing grooves corresponding to the at least one or more first fixing protrusion and the at least one or more second fixing protrusion are formed on an inner surface of the fourth member.

* * * * *